(12) United States Patent
Tanaka et al.

(10) Patent No.: US 7,064,101 B2
(45) Date of Patent: Jun. 20, 2006

(54) STABLE ASTAXANTHIN-CONTAINING POWDERY COMPOSITIONS AND PROCESS FOR PRODUCING THE SAME

(75) Inventors: Nobukazu Tanaka, Toyama (JP);
Tadashi Fukami, Toyama (JP);
Terumasa Hosokawa, Toyama (JP);
Takeshi Shishido, Toyama (JP)

(73) Assignee: Fuji Chemical Industry Co., Ltd., Toyoma (JP)

( * ) Notice: Subject to any disclaimer, the term of this patent is extended or adjusted under 35 U.S.C. 154(b) by 184 days.

(21) Appl. No.: 10/472,679

(22) PCT Filed: Mar. 22, 2002

(86) PCT No.: PCT/JP02/02789

§ 371 (c)(1),
(2), (4) Date: Sep. 18, 2003

(87) PCT Pub. No.: WO02/77105

PCT Pub. Date: Mar. 10, 2002

(65) Prior Publication Data
US 2004/0091524 A1    May 13, 2004

(30) Foreign Application Priority Data
Mar. 22, 2001    (JP)    .............................. 2001-081998

(51) Int. Cl.
*C11D 1/66*    (2006.01)
*C11D 11/02*    (2006.01)
*C11D 17/06*    (2006.01)
*C09K 15/06*    (2006.01)
*C09K 15/34*    (2006.01)

(52) U.S. Cl. ...................... 510/446; 510/452; 510/461; 510/505; 424/489

(58) Field of Classification Search ................ 510/446, 510/452, 461, 505; 424/489
See application file for complete search history.

(56) References Cited

FOREIGN PATENT DOCUMENTS

| | | |
|---|---|---|
| EP | 0 807 431 A2 | 11/1997 |
| EP | 807431 * | 11/1997 |
| GB | 2 301 587 A | 12/1996 |
| JP | 07-171383 A | 7/1995 |
| JP | 10195325 * | 1/1998 |
| JP | 10-195325 A | 7/1998 |
| JP | 10-316877 A | 12/1998 |

* cited by examiner

*Primary Examiner*—Brian P. Mruk
(74) *Attorney, Agent, or Firm*—Flynn, Thiel, Boutell & Tanis, P.C.

(57) ABSTRACT

The present invention relates to a stable astaxanthin-containing powdery composition which is obtained by drying a suspension containing a ground Haematococcus alga containing astaxanthin, a surfactant, an antioxidant, an excipient and water and to a process for preparing the same.

According to the present invention, there can be provided an astaxanthin-containing powdery composition wherein astaxanthin present in Haematococcus alga has been efficiently stabilized to improve its storage stability for a long term and which is excellent in flowability as a powder, easy to handle and can be easily subjected to solvent extraction without degrading the astaxanthin.

10 Claims, No Drawings

STABLE ASTAXANTHIN-CONTAINING POWDERY COMPOSITIONS AND PROCESS FOR PRODUCING THE SAME

TECHNICAL FIELD

The present invention relates to a stable astaxanthin-containing powdery composition which is obtained by drying a suspension comprising a ground Haematococcus alga containing astaxanthin, a surfactant, an antioxidant, an excipient and water and to a process for preparing the same. More particularly, it relates to an astaxanthin-containing powdery composition wherein the astaxanthin present in Haematococcus alga has been efficiently stabilized to improve its storage stability for a long term and which is excellent in flowability as a powder, easy to handle and the astaxanthin can be easily extracted with a solvent without being degraded and to a process for preparing the same.

BACKGROUND ART

Astaxanthin is known as a red carotenoid which has a wide distribution in crustaceans such as krill, shrimp, crab and the like, the body surface of porgy, the muscle of salmon, fish eggs such as salmon roe and the like, in yeast, algae or genetic recombined microorganisms. Astaxanthin is used as a color tone-improving agent and reviver for cultivated fishes and shellfishes and it is also reported to act as an antioxidant, etc. (Enju Shimizu and Wataru Miki: "Carotinoids of Marine Organisms", edited by Wataru Miki, Koseisha Koseikaku in the 5th year of Heisei) and has been applied to food additives, cosmetics and so on. This astaxanthin can be obtained from plants, genus Falfa yeast cell body, seaweeds, bacteria, or crustaceans by extraction techniques. Particularly, a process for obtaining astaxanthin from the green algae of Haematococcus is in an extremely advantageous position as a process for supplying astaxanthin derived from a natural origin since there was developed a process for cultivating Haematococcus containing a high concentration of astaxanthin in large quantities and stably. Some processes are reported for extracting astaxanthin from this Haematococcus alga. Usually, this Haematococcus is covered with the cell walls enclosed by a gelatinous and sticky capsule, and hence the cell walls of the algae are ruptured (broken) for the purpose of extracting astaxanthin. As one of the processes for rupturing (breaking) the cell walls of the alga, the process for subjecting the algae to physical rupture treatment is known. Specifically, the following processes are reported: a process for grinding down the encysted Haematococcus after a preliminary drying with liquid nitrogen (WO89/06910), a process for rupturing the cell walls by freeze drying the encysted Haematococcus cells at a temperature below −50° C. followed by the addition of sodium chloride and comminuting the cells (French Patent Application No. 2,703,692), the recovery of astaxanthin carotenoid pigment from Haematococcus algae wherein the cell walls of algae are ruptured by the application of turbulent flow under a high pressure and the ruptured cell walls are dried and astaxanthins are extracted with an organic solvent (Japanese Patent Application Laid-Open No. Hei 9-111139) and a process for grinding Haematococcus in a dry encysted state to fine powders having an average particle size below 10 μm (Japanese Patent Application Kohyo No. Hei 02-503632). As a process for extracting a lipid containing astaxanthins from the ruptured alga which was obtained by these processes, a process is known for extracting it with an organic solvent such as ethanol, acetone, ether, chloroform, methylene chloride, hexane or the like, distilling off the solvent from the extract liquor to obtain an oil containing astaxanthins.

It became possible to supply an astaxanthins-containing Haematococcus alga in large quantities by a cultivation process, and consequently a problem occurred in the preservation management of Haematococcus alga until the extraction procedures of astaxanthin has been finished. Although Haematococcus algae themselves can be preserved stably by preserving them at low temperature, large-scale storage facilities are needed in order to preserve them in large quantities. Also, when large quantities of Haematococcus alga was subjected to rupture treatment, the resultant suspension (slurry) of ground Haematococcus caused a bad operability due to putrefaction. In this case, refrigeration facilities for preventing the putrefaction and maintenance and management costs for them are needed. As a result, these are not economical due to the complicated operations. Furthermore, there was a problem that the astaxanthin present in the ground Haematococcus alga degraded when contacted with oxygen, thus its content decreased.

DISCLOSURE OF THE INVENTION

An object of the present invention is to provide an astaxanthin-containing powdery composition wherein astaxanthin present in Haematococcus algae has been efficiently stabilized to improve its storage stability for a long term and which is excellent in flowability as a powder, easy to handle and can be easily subjected to solvent extraction without degrading astaxanthin and to provide a process for preparing the same.

As a result of having ardently studied to solve the above object, the present inventors have found that by drying the ground Haematococcus under a specific condition to a powdery composition, astaxanthin which is an effective ingredient can be stored in a stable state in the powders, and have completed the present invention.

That is, the present invention is a powdery composition which is obtained by drying a suspension comprising a ground Haematococcus alga containing astaxanthin, a surfactant, an antioxidant, an excipient and water, said powdery composition having a high granule-forming property, being spherical, highly flowable, not high in bulk (specific volume), heavy-duty and easy to handle, its preparation process and a process for an organic solvent extraction of astaxanthin using this powdery composition. This process using the powdery composition is an industrially advantageous extraction process since water does not coexist in the stage of the extraction step so that the extraction efficiency becomes good. More specifically, the invention involves a powdery composition which is obtained by drying a suspension comprising a ground Haematococcus alga containing astaxanthin, a surfactant, an antioxidant, an excipient and water, the invention also is the powdery composition wherein said surfactant is a water-soluble one wherein an HLB value is above 7.0, the invention also is the powdery composition wherein said surfactant is one or more members selected from the group consisting of glycerin fatty acid ester, sucrose fatty acid ester, sorbitan fatty acid ester and propylene glycol fatty acid ester, the invention also is the powdery composition wherein said antioxidant is one or more members selected from the group consisting of vitamin E (tocopherol), rosemary extract, tocotrienol and vitamin C, the invention also is the powdery composition wherein said excipient is one or more of inorganic powders selected from the group consisting of silicic anhydride, calcium hydrogen phosphate, calcium silicate and calcium phosphate, the invention also is the powdery composition wherein drying has been conducted by a spray drying process, the invention also is a process for preparing a powdery composition containing astaxanthin which comprises drying a suspension comprising a ground Haematococcus alga containing astaxanthin, an antioxidant, an excipient and water, the invention also is a preparation process wherein drying is conducted by a spray drying process, and the invention also is a process for recovering astaxanthin from the above-described powdery composition by an organic solvent extraction.

The powdery composition of the present invention is illustrated specifically.

The powdery composition of the present invention is a powdery composition containing astaxanthin which is obtained by drying a suspension comprising a ground Haematococcus alga containing astaxanthin, a surfactant, an antioxidant, an excipient and water.

The above-described powdery composition, for example the powders obtained by drying the suspension wherein soft silicic anhydride was used as the excipient, are spherical, highly flowable and heavy-duty ones having a specific volume in the vicinity of 1.5–3.0 ml/g, preferably 1.8–2.5 ml/g, more preferably 2.0 ml/g. This powder is excellent in flowability, easy to handle and can be obtained in a high yield without adhering to the walls of a dryer during spray drying. In addition the astaxanthin present in this powdery composition exists stably without being degraded, as stated later.

The Haematococcus alga for use in the present invention contains various components. For example, as the ratios of the components present in the alga, which was allowed to dry according to the conventional process, there may be taken one containing 0.3–10% by weight of astaxanthin components, 20–60% by weight of crude proteins, 5–50% by weight of crude fats, 5–50% by weight of carbohydrates, 1–10% by weight of crude ash and 0.5–5% by weight of water.

The content of astaxanthin components in the Haematococcus alga is usually 0.3–10% by weight as shown above. The composition may be varied depending on the cultivation condition for alga and is not limited particularly. For example, it is 0–10% by weight of free astaxanthin form, 50–90% by weight of astaxanthin monoester and 10–30% by weight of astaxanthin diester. The content of astaxanthin components may be adequately selected depending on the object for preparing the powders and is not limited particularly.

The rupturing step of the Haematococcus alga is designed to rupture the alga to such an extent that all the contents in the cell can be contacted with a solvent. This step may be conducted with e.g. a homogenizer and a grinder according to the conventional process. Although the rupturing state of the alga is more preferable as it is fine, usually the particle size may be below 10 μm.

The surfactant is used for emulsifying the oil containing astaxanthin liberated from the Haematococcus alga by the rupturing operation. The content of the surfactant may be varied depending on the kind of surfactant and is not limited particularly. In the case of, for example decaglyceryl monolaurate ("decaglyn" a trade name, a product of Nikko Chemical Co., Ltd.), it is in the range of usually 0.1–6.0 parts by weight, preferably 0.5–5.0 parts by weight, more preferably 0.5–2.0 parts by weight based on 100 parts by weight of Haematococcus alga.

The antioxidant is added for stabilizing the astaxanthin present in the powders obtained by the present process and for preventing astaxanthin from being degraded in the extraction step as stated later.

The content of the antioxidant may be varied depending on the kind of antioxidant and is not limited particularly. However, it is in the range of usually 0.1–6.0 parts by weight, preferably 0.5–5.0 parts by weight, more preferably 0.5–2.0 parts by weight based on 100 parts by weight of Haematococcus alga.

The excipient stabilizes the shape of the powders obtained by the present process, adsorbs the oil containing astaxanthin liberated from Haematococcus alga by the rupturing operation, and stabilizes the astaxanthin present in the powders together with the coexisting antioxidant.

As the excipient, there may be used inorganic powders such as porous calcium silicate, soft silicic anhydride, calcium hydrogen phosphate, calcium phosphate, diatomaceous earth, sodium sulfate, powders of shells (powders of shells such as oyster and the like), calcium carbonate, talc, powdered coral, zeolite, silica gel, activated carbon and so on. Preferably, porous calcium silicate, soft silicic anhydride, calcium hydrogen phosphate, calcium phosphate and the like may be taken. Also, one or more kinds of these excipients may be used.

The content of the excipient in the astaxanthin-containing powders involved in the present invention may be varied depending on the kind of excipient, the extent of rupture of the alga, the amount of water to be used in the suspension, the kind of surfactant, etc., and is not limited particularly. In the case of, for example porous calcium silicate ("Florite RE", a trade name), its content is in the range of usually 1–99 parts by weight, preferably 5–99 parts by weight, more preferably 5–50 parts by weight based on 100 parts by weight of Haematococcus alga while in either the case of soft silicic anhydride ("Adsolider 101", a trade name, a product of Freund Industrial Co., Ltd.) or soft silicic anhydride ("SYLOPAGE", a trade name, a product of Freund Industrial Co., Ltd.), its content is in the range of usually 1–99 parts by weight, preferably 10–90 parts by weight, more preferably 10–50 parts by weight based on 100 parts by weight of Haematococcus alga, and in the case of anhydrous calcium hydrogen phosphate ("Fujicalin", a trade name, a product of Fiji Chemical Industry Co., Ltd.) its content is in the range of usually 1–99 parts by weight, preferably 15–99 parts by weight, more preferably 15–50 parts by weight based on 100 parts by weight of Haematococcus alga.

Since these excipients have a large specific surface area and are porous materials or crystals wherein scaly crystals have a card house structure like "Fujicalin" (their oil absorption functions are considered to be great), a tendency to reduce their amount to be used was recognized.

The astaxanthin-containing powdery composition which may be obtained by the above-described process can be preserved stably at a low temperature of 4–15° C., preferably 4–10° C. The costs such as management expense or the like can be greatly saved in comparison with the prior art processes wherein the ground alga has been stored at −20° C. or less. Of course, if the powders which may be obtained by the present invention are preserved at a temperature lower than 4° C., they are more stable.

The preferred embodiment of the present invention is a process for preparing an astaxanthin-containing powdery composition which comprises emulsifying a ground Haematococcus alga containing astaxanthin in a water medium in the coexistence of a surfactant and an antioxidant, adding an excipient while keeping the ground alga in an emulsified state and spray drying the suspension prepared thusly.

The Haematococcus alga for use in the present invention may be any green alga so long as it is Haematococcus green alga which produces an astaxanthin. Specifically, Haematococcus pluvialis, Haematococcus lacustris, Haematococcus capensis, Haematococcus droebakensis, Haematococcus zimbabwiensis, etc. may be taken. More specifically, green algae such as Haematococcus pluvialis NIES 144, Haematococcus lacustris ATCC 30402, ATCC 30453, IAM C296, IAM 392, IAM 393, IAM 394, IAM 399, Haematococcus capensis UTEX 1023, Haematococcus droebakensis UTEX 55, Haematococcus zimbabwiensis UTEX 1758, etc. may be taken.

The process for cultivating Haematococcus green algae is not limited particularly and there may be used any of the known processes by which the vegetative cell can be prepared, for example, a process wherein green algae Haematococcus pluvialis may be heterotrophically cultivated in light using an organic substance such as acetic acid as a carbon source, or autotrophically cultivated in a dark place using carbon dioxide as a carbon source, or heterotrophically and autotrophically proliferated in light using both an organic substance such as acetic acid and carbon dioxide as a carbon source [Kobayashi et al; J. Ferment. Bioeng., 74, 17 (1992)].

As a cultivation process for obtaining Haematococcus algae having a high content of astaxanthin, there is disclosed a cultivation process using a hermetic type of dome-like, conical or cylindrical cultivation apparatus wherein culture incubators are equipped with an optionally movable gas ejector (WO 99/50384). The astaxanthin content in Haematococcus alga for use in the present invention is not limited particularly. However, a high astaxanthin content is preferable since, as the astaxanthin content is high, the extraction efficiency of astaxanthin after pulverization become better.

The Haematococcus alga for use in the present invention may be obtained from the cultivation liquor e.g. by filtration according to the conventional manner. The Haematococcus alga to be ruptured may be employed in a wet state (the amount used in this case is estimated in terms of the dry product) or otherwise the Haematococcus alga obtained by filtration and an antioxidant are suspended in water and the resulting suspension is allowed to dry by spray drying, etc., thus the obtained dry product may be used.

As a process for rupturing the Haematococcus alga, the alga is suspended in water and the resultant suspension is subjected to wet rupturing with a grinder, for example "Micros MIC-5NZ" (Zirconia ceramics) (a trade name, a product of Nara Machinery Co., Ltd.), "DYNO-MILL" (a trade name, Switzerland, a product of Willy A. Bachofen AG Company) or the like whereby the ruptured product may be prepared.

The range of the particle size in the ground Haematococcus alga is not limited particularly. However, it is preferable that the Haematococcus alga is ruptured to particles below 10 μm since as the particles become fine, the extraction efficiency of astaxanthin from the powdery composition which is obtained by the present process becomes better.

As a surfactant, there is used a water soluble one having an HLB value above 7.0, preferably above 10, more preferably above 15. Specifically, suitable are a polyglycerin fatty acid ester, glycerin fatty acid ester, sucrose fatty acid ester, sorbitan fatty acid ester, propylene glycol fatty acid ester, preferably a polyglycerin fatty acid ester, glycerin fatty acid ester, sucrose fatty acid ester and so on, more preferably a polyglycerin fatty acid ester.

As examples of a polyglycerin fatty acid ester, there may be taken products manufactured by Nikko Chemicals Co., Ltd. as shown below: decaglyceryl monolaurate (HLB 15.5), decaglyceryl monomyristerate (HLB 14), decaglyceryl monostearate (HLB 12.0), decaglyceryl monooleate (HLB 12.0), decaglyceryl monolinolenate (HLB 12.0), decaglyceryl monoisostearate (HLB 12.0), decaglyceryl distearate (HLB 9.5), decaglyceryl dioleate (HLB 10.0), decaglyceryl diisostearate (HLB 10.0), decaglyceryl tristearate (HLB 7.5), decaglyceryl trioleate (HLB 7.0), decaglyceryl trioisostearate (HLB 7.0), and the like. Preferred is decaglyceryl monolaurate which is clearly soluble in water ("Decaglyn 1-L", a trade name HLB 15.5, a product of Nikko Chemicals Co., Ltd.)

As examples of sucrose fatty acid ester, there may be taken "S-1670", "LWA-1570" (products of Mitsubishi Chemicals Corporation), "DK-ESTER SS", "DK-ESTER F-160" (products of Dai-ichi Kogyo Seiyaku Co., Ltd.), and the like. Among the above surfactants, more preferable is one which may be utilized as a food additive.

As examples of an antioxidant, there may be taken vitamin E (tocopherol), rosemary extract (a trade name "Pap'Stab", a product of NATUREX Inc.), tocotrienol, vitamin C, glutathion, phytic acid, catechinic acid, flavonoids, β-carotene, and the like. Preferable are vitamin E, rosemary extract, tocotrienol and vitamin C.

In the present invention, in addition to the process for preparing a suspension wherein the ground Haematococcus alga was emulsified in a water medium in the presence of a surfactant and an antioxidant, while the alga is in an emulsified state, an excipient is added thereto and, thereby, a suspension is prepared, Haematococcus alga (not ground) is dispersed in the water medium in the presence of a surfactant, an antioxidant and an excipient, and the resultant dispersion is subjected to rupture treatment whereby the ground Haematococcus alga-containing suspension to be dried may be prepared. In this case, the powders of the present invention can be stabilized in two steps as shown below.

(The first step)

Water, a surfactant and an antioxidant are added to a tank and dispersed or dissolved under stirring and thereafter a dry product of Haematococcus alga is added thereto and the mixture is stirred whereby a suspension is prepared.

Although the temperature of the suspension is not limited particularly, it is in the range of usually 0–40° C., preferably 4–30° C., more preferably 4–25° C.

The obtained suspension can be subjected to rupture treatment using a commercial grinder, for example "Micros MIC-5NZ" (Zirconia ceramics) (a trade name, a product of Nara Machinery Co., Ltd.), "DYNO-MILL", or the like. The rupture condition is that a rotation number of a rotor is about 800 to about 1,600 rotation/min., preferably about 1,200 rotation/min., preferably under an atmosphere of an inert gas such as nitrogen or the like.

The feed amount of the suspension to a grinder may be 0.5–1.0 L/min. preferably 0.75–0.80 L/min. The temperature within the apparatus is preferably a lower temperature in the range of usually 4–60° C., preferably 25–55° C. Even when it is in the range of 40–55° C., there is no problem.

The rupture time may be varied depending on the respective amounts used and kinds of Haematococcus alga to be ruptured, the surfactant and the antioxidant, the temperature at which the rupture treatment is conducted, and the like. However, it is usually 1–10 hours, preferably 1–8 hours.

Although the addition time of the surfactant is not limited particularly, preferably it is added before the beginning of the rupturing.

Although the addition time of the antioxidant is not limited particularly since the rupturing itself is conducted under an atmosphere of an inert gas, preferably it can be added before the beginning of the rupturing. The treatment time may be varied depending on the amount of the staring materials, the amount to be treated by a grinder and the like and it is not limited particularly. However, it is 1–8 hours.

In the present process, the addition order of the ground Haematococcus alga containing astaxanthin, a surfactant, an antioxidant, an excipient and water is not limited particularly. When compared among the embodiments of the present invention, however, it is preferable that the excipient is added to the suspension after the Haematococcus alga has been ruptured since the abrasion of the grinder is small. In this case, the concentration of the suspension is 5–40% by weight, preferably 20–35% by weight.

It became clear that by this rupture treatment, almost no astaxanthin present in the suspension was degraded as compared with the starting material. This suspension may be subjected to the drying treatment immediately when it was prepared. Also, in the case where it cannot be immediately subjected to the drying treatment, it may be stored temporarily at a temperature below 10° C. for use.

As the drying treatment, it may be carried out for example, by spray drying, flash drying, belt drying, cool air drying, drum drying, and the like according to the usual process.

Next, an example of spray drying process is illustrated.

(The second step)

The spray drying may be conducted, for example at the inlet temperature range of 200–220° C. and the outlet temperature range of 95–105° C. of a spray drier according to the conventional process.

The powders which may be obtained by spray drying have a water content below 4%, high granule-forming property, are spherical and well flowable. It is preferable that they are heavy-duty powders having a bulk (specific volume) of 1.5–3.0 ml/g, preferably 1.8–2.2 ml/g, more preferably about 2.0 ml/g, due to their easy handling property.

The Best Mode For Carrying Out The Invention

The following Referential Examples and Examples illustrate the present invention.

REFERENTIAL EXAMPLE 1

75.0 Kg of water, 0.45 kg of decaglyceryl monolaurate ("Decaglyn 1-L" a trade name, a product of Nikko Chemicals Co., Ltd.) and 0.45 kg of rosemary extract ("Pap'Stab", a trade name, a product of NATUREX Inc.) were added to a tank, dispersed or dissolved under stirring, and thereafter 18.0 kg of Haematococcus alga dry product was added and followed by stirring so thereby a suspension was prepared (the temperature of the suspension at this time was 24–25° C.). The obtained suspension was subjected to the rupturing treatment with a grinder ("Micros MIC-5NZ" (Zirconia ceramics) (a trade name, a product of Nara Machinery Co., Ltd.), "DYNO-MILL", or the like.

The rupturing condition: The suspension was subjected to the rupture treatment for 130 minutes to obtain 95.0 kg (20 kg of solid content) of a final suspension (the rate of rupture at this time: 92.5%) by passing through the grinder wherein the rotation number of a rotor, the amount fed of the suspension and the temperature were kept so as to become 1,200 rotations/min., 0.75–0.80 L/min. and 42–49° C., respectively under an atmosphere of nitrogen.

This suspension can be kept in a stable state even when stored below 10° C., and no change was seen in the appearance even after 17–20 hours has elapsed.

REFERENTIAL EXAMPLE 2

172.0 Kg of water, 1.025 kg of decaglyceryl monolaurate ("Decaglyn 1-L" a trade name, a product of Nikko Chemicals Co., Ltd.) and 1.025 kg of rosemary extract ("Pap'Stab", a trade name, a product of NATUREX Inc.) were added to a tank, dispersed or dissolved under a stirring, and thereafter 41.0 kg of dry product of Haematococcus alga was added and followed by stirring so thereby a suspension was prepared (the temperature of the suspension at this time was 24–25° C.). The obtained suspension was subjected to rupturing treatment for 4.5 hours with a grinder ("Micros MIC-5NZ" (Zirconia ceramics) (a trade name, a product of Nara Machinery Co., Ltd.), "DYNO-MILL", or the like by passing through the grinder under the rupturing condition that the rotation number of a rotor was 1,200 rotations/min., and the amount fed of the suspension was 0.75–0.80 L/min. and the temperature within the apparatus was 45.8–51.9° C. under an atmosphere of nitrogen. There was obtained 217.7 kg (43.05 kg of solid content) of a final suspension.

This suspension can be kept in a stable state even when stored below 10° C., and no change was seen in the appearance even after 17–20 hours has elapsed.

EXAMPLE 1

11.8 Kg of soft silicic anhydride (Adsolider 101", a trade name, a product of Freund Industrial Co., Ltd.) was suspended in 180 liters (L) of water and 308.95 kg of a mixture of the respective suspensions obtained in Referential Examples 1 and 2 (an average rate of rupture of 91.2%) was added thereto under a stirring [total weight amount of 500 Kg (a solids content of 15% by weight)]. The obtained suspension was spray dried (drying conditions; an inlet temperature of 210° C., an outlet temperature of 100–102° C. and a rotation number of the atomizer of 9,000) whereby 64.2 kg of powders (43.6 kg of CH product and 20.6 kg of CY product) were obtained (yield: 87.1%).

The above-described powders were free-flowable and spherical particles, and their specific volumes as powders themselves was 1.82 mL/g while those as the tapped product was 1.47 ml/g, the water content being 2.24%, the angle of repose being 360 and the particle distribution consists of ~30th class (0.1%), 30–60th class (0.6%), 60–100th class (1.9%), 100–200th class (62.1%) and 200th class ~(35.4%). These powders were ones containing 2.81% by weight of astaxanthin (in terms of free form).

EXAMPLE 2

0.12 Kg of porous calcium silicate ("Florite RE", a trade name, a product of Tokuyama Corp., specific calcium silicate) was suspended in 1.80 liter (L) of water and 3.09 kg of a mixture of the respective suspensions obtained in Referential Examples 1 and 2 (an average rate of rupture of 91.2%) was added thereto under stirring [total weight amount of 5 Kg (the solid content of 15% by weight)]. The obtained suspension was dried with a spray drier "MMSD" (a trade name, a product of Niro Japan Co., Ltd.) (drying condition; an inlet temperature of 210° C., an outlet temperature of 100–102° C.) whereby 0.516 kg of powders was obtained (yield: 70.1%). The above-described powders were free-flowable and spherical particles. These powders contained 2.80% by weight of astaxanthin (in terms of free form).

EXAMPLE 3

0.12 Kg of calcium hydrogen phosphate ("Fujicalin", a trade name, a product of Fiji Chemical Industry Co., Ltd.) was suspended in 1.80 liter (L) of water and 3.09 kg of a mixture of the respective suspensions obtained in Referential Examples 1 and 2 (an average rate of rupture of 91.2%) was added thereto under stirring [total weight amount of 5 Kg (solid content of 15% by weight)]. The obtained suspension was dried with a spray drier "MMSD" (a trade name, a product of Niro Japan Co., Ltd.) (drying condition: an inlet temperature of 210° C., an outlet temperature of 100–102° C.) whereby 0.51 kg of powders was obtained (yield: 69.2%). The above-described powders were free-flowable and spherical particles. These powders contained 2.80% by weight of astaxanthin (in terms of free form).

EXAMPLE 4

1.2 g of soft silicic anhydride ("Adsolider 101", a product of Freund Industrial Co., Ltd.) was suspended in 18 ml of water and 30.9 g of a mixture of the respective suspensions obtained in Referential Examples 1 and 2 (an average rate of rupture of 91.2%) was added thereto under stirring [total weight amount of 50 g (solid content of 15% by weight)]. By removing water under a reduced pressure, 7.30 g of powders were obtained (yield: 99%).

COMPARATIVE EXAMPLES 1–4

Using each of the emulsifiable starches "HICAP100" and "N-CREAMER" in place of decaglyceryl monolaurate ("Decaglyn 1-L" a trade name, a product of Nikko Chemicals Co., Ltd.) in Referential Example 1 or 2, the similar procedure as in Referential Examples 1–2 was conducted to prepare suspensions.

Each of the above-described suspensions was spray dried in the similar manner as in Example 1 without using soft silicic anhydride ("Adsolider 101", a product of Freund Industrial Co., Ltd.) which was used in Example 1 to obtain powders. These are indicated as Comparative Examples 1–4.

The results are shown in table 1 below.

TABLE 1

| Name of item | Comparative Example 1 | Comparative Example 2 | Comparative Example 3 | Comparative Example 4 |
| --- | --- | --- | --- | --- |
| Ruptured Haematococcus Product (Solid matters) | 350 L (70 kg) | 325 L (65 kg) | 275 L (60 kg) | 350 L (70 kg) |
| "HICAP100" | 28.0 Kg | 33.0 kg | 43.0 kg | 13.0 kg |
| "N-CREAMER" | — | — | — | 15.0 kg |
| "Pap' Stab" | 2.0 | 2.0 | 2.0 | 2.0 |

Each of the suspensions of Comparative Examples 1–4 in table 1 was spray dried under the conditions as shown below for comparison in the yield (%) and the residual rate of astaxanthin.

Spray drying of the suspension in the above-described Comparative Example 1:
Inlet temperature: 240° C., outlet temperature: 104–109° C., yield: 59.8%, the astaxanthin content (%) before spray drying: 2.18%, the astaxanthin content (%) after spray drying: 2.13%, the residual rate of astaxanthin: 97.5%

Spray drying of the suspension in the above-described Comparative Example 2:
Inlet temperature: 240° C., outlet temperature: 104–108° C., yield: 81.4%, the astaxanthin content (%) before spray drying: 2.03%, the astaxanthin content (%) after spray drying: 1.93%, the residual rate of astaxanthin: 95.2%

Spray drying of the suspension in the above-described Comparative Example 3:
Inlet temperature: 240° C., outlet temperature: 101–104° C., yield: 76.3%, the astaxanthin content (%) before spray drying: 2.18%, the astaxanthin content (%) after spray drying: 2.05%, the residual rate of astaxanthin: 93.9%

Spray drying of the suspension in the above-described Comparative Example 4:
Inlet temperature: 240° C., outlet temperature: 102–107° C., yield: 82.1%, the astaxanthin content (%) before spray drying: 2.18%, the astaxanthin content (%) after spray drying: 2.05%, the residual rate of astaxanthin: 93.9%

From the foregoing results, the yields of the respective powders in Comparative Examples 1–4 were 59.8–81.4%, but these powders were easily aggregated and had a low flowability.

EXPERIMENTAL EXAMPLE 1

Stability of powders

The accelerated stability was examined with respect to the powders obtained in Example 1 by a method wherein the amount of astaxanthin present in the powders was tested (for 2–4 hours) at 80° C. under an oxygen replacement.

TABLE 2

| Time (hr) | Astaxanthin content (%) | Residual rate of astaxanthin (%) |
| --- | --- | --- |
| 0 | 2.81 | 100.0 |
| 2 | 2.66 | 94.9 |
| 4 | 2.53 | 90.2 |

The accelerated stability was examined with respect to the powders obtained in Comparative Examples 1–4 by a method wherein the amount of astaxanthin present in the powders was tested (for 2–4 hours) at 80° C. under an oxygen replacement.

TABLE 3

| | Residual rate of astaxanthin (%) | | | |
| --- | --- | --- | --- | --- |
| Time (hr) | Comparative Example 1 | Comparative Example 2 | Comparative Example 3 | Comparative Example 4 |
| 2 | 82.4 | 77.8 | 74.4 | 77.7 |
| 4 | 64.2 | 56.9 | 52.5 | 60.6 |

The powders having a high flowability could be obtained in a high yield by the preparation process of the present invention.

The amount adhered of the powder to the inner wall of a spray drier was small, the residual amount of astaxanthin after 4 hours in the accelerated test conducted at 80° C. under an oxygen replacement was 90.2%, thus they were very stable. Contrary thereto, in the case of the powders obtained by the prior art process using a starch, the yield was low and the stability in the accelerated test conducted at 80° C. under an oxygen replacement were low, and the inner parts of the devices located within the spray drier were in a red-colored state due to the bleeding out of astaxanthin from them.

The astaxanthin-containing powdery composition of the present invention, which is obtained by drying a suspension comprising a ground Haematococcus alga containing astaxanthin, an antioxidant, an excipient and water, is stable in itself. In addition, as a glidant, for example, silicic anhydride from among the foregoing excipients may be additionally incorporated in an amount of 1–10%, preferably 1–5% per weight amount of the powders. By the additional incorporation of the glidant, in some cases the stability of the powders may be further improved and it becomes easy to handle the powders during extraction procedures stated later.

With respect to the stability of astaxanthin present in the powders which are obtained by the present invention, the spray dried product has better stability than the dried product of the mixture.

By the present process, that is, by using inorganic powdery excipients such as silicic anhydride and the like during the drying, the recovery efficiency of the powders during the drying increases and therefore the residual amount adhered to the devices decreases. Consequently, since the amount of washing water for the devices can be reduced, the treatment of the washing drainage becomes easy and the washing treatment can be carried out in a short time, thus the operating efficiency is good.

Next, (1) the operation process of extraction and absorbance measurement for determining the astaxanthin liberated from the ruptured Haematococcus alga cell walls and (2) the operation process of absorbance measurement for determining the astaxanthin present in an oil which is obtained by the organic solvent extraction of the astaxanthin-containing powders obtained by the present invention.

The extraction of astaxanthin from the ruptured alga cell walls and the operation of absorbance measurement. The quantitative process (total astaxanthin substances): (the free form and absorptiometry)

About 50 mg of the present product was weighed accurately and suspended in 1 ml of water and the resultant suspension was subjected to supersonic wave treatment at 40–50° C. for a minute, 10 ml of acetone was further added and followed by supersonic wave treatment for 5 minutes. The supernatant liquid obtained by centrifugal separation was placed in a 100 ml measuring flask. The residue was added to 10 ml of acetone and then subjected to supersonic wave treatment at 40–50° C. for 5 minutes and the supernatant liquid obtained by centrifugal separation was placed in the same measuring flask as above. Furthermore, the similar procedure was repeated 2–3 times with 10 ml of acetone each time until the supernatant liquid became colorless. The obtained supernatant liquid was placed in the same measuring flask as above, and acetone was added thereto to make 100 ml of solution accurately. 10 Ml of this solution was weighed accurately and acetone was added thereto to make 20 ml of solution accurately which was designated as the sample solution. Acetone was designated as the control for the sample solution. A series of tests were conducted by absorptiometry to measure the absorbance A at a wavelength of 475 nm.

The amount of astaxanthin ($C_{40}H_52O_4$) (%)=($A$×1000×200/(2100×$S$)

A: The absorbance of the sample solution
S: The amount collected of sample (mg)
2100: The coefficient in acetone The extraction of astaxanthin from the astaxanthin-containing powder (AstaREAL powder) and the operation of absorbance measurement The quantitative process (total astaxanthin substances): (the free form and absorptiometry)

About 50 mg of the present product was weighed accurately and suspended in 1 ml of water and the resultant suspension was subjected to supersonic wave treatment at 40–50° C. for a minute, 10 ml of acetone was further added and followed by supersonic wave treatment for 5 minutes. The supernatant liquid obtained by centrifugal separation was placed in a 100 ml measuring flask. To the residue was added 10 ml of acetone and then subjected to supersonic wave treatment at 40–50° C. for 5 minutes and the supernatant liquid obtained by centrifugal separation was placed in the same measuring flask as above. Furthermore, the similar procedure was repeated 2–3 times with 10 ml of acetone each time until the supernatant liquid became colorless. The obtained supernatant liquid was placed in the same measuring flask as above, and acetone was added thereto to make 100 ml of solution accurately. 10 Ml of this solution was weighed accurately and acetone was added thereto to make 30 ml of solution accurately which was designated as the sample solution. Acetone was designated as the control for the sample solution. A series of tests were conducted by absorptiometry to measure the absorbance A at a wavelength of 475 nm.

The amount of total astaxanthin (%)=($A$×1000×300/(2100×$S$) (The terms "total astaxanthin" mean a mixture of the free form and ester form.)

A: The absorbance of the sample solution
S: The amount collected of sample (mg)
2100: The coefficient in acetone As a process for recovering astaxanthin from the astaxanthin-containing powdery composition of the present invention, astaxanthin is fat-soluble and hence, for example, an organic solvent extraction, supercritical extraction or the like is possible.

As examples of an organic solvent, there may be taken ones such as acetone, ethyl acetate, methanol, ethanol, ether, chloroform, methylene chloride, n-hexane and the like. After the extraction, the solvent is distilled off according to a conventional process to thereby obtain an oil containing astaxanthin.

It may also be extracted with one kind or a mixed solution of two or more kinds of these organic solvents. Also, for the purpose of allowing the astaxanthin extracted to be contained in an oil directly, it can be extracted using a vegetable oil or a mineral oil as the extraction solvent.

Also, astaxanthin may be quantitatively recovered by supercritical extraction (carbon dioxide).

TEST EXAMPLE 1

Recovery of Astaxanthin

To 1 kg of the powders (the content of astaxanthin: 2.81%) obtained in the above-described Example 1 was added 6.5 L of acetone and then stirred at 60° C. for an hour. After insoluble matters were removed by filtration, the filtrate was distilled under a reduced pressure to obtain an oily residue (the recovery rate of astaxanthin was quantitative).

TEST EXAMPLE 2

Recovery of Astaxanthin

To 1 kg of the powders (the content of astaxanthin: 2.81%) obtained in the above-described Example 1 was added 6.5 L of ethyl acetate and then stirred at 60° C. for an hour. After insoluble matters were removed by filtration, the filtrate was distilled under a reduced pressure to obtain an oily residue (the recovery rate of astaxanthin was quantitative).

TEST EXAMPLE 3

Recovery of Astaxanthin

To 100 g of the powders (the content of astaxanthin: 2.81%) obtained in the above-described Example 2 was added 650 ml of ethyl acetate and then stirred at 60° C. for an hour. After insoluble matters were removed by filtration, the filtrate was distilled under a reduced pressure to obtain an oily residue (the recovery rate of astaxanthin was quantitative).

TEST EXAMPLE 4

Recovery of Astaxanthin

To 100 g of the powders (the content of astaxanthin: 2.81%) obtained in the above-described Example 3 was added 700 ml of acetone and then stirred at 60° C. for an hour. After insoluble matters were removed by filtration, the filtrate was distilled under a reduced pressure to obtain an oily residue (the recovery rate of astaxanthin was quantitative).

It can be understood that the powdery composition of the present invention is subjected to an organic solvent extraction and the extraction liquor is concentrated whereby astaxanthin may be efficiently recovered.

The extraction efficiency was in the order of spray dried product>mixed product>>mere ruptured product.

The above-described recovery product may be further treated by means such as a molecular distillation process depending on the necessity whereby the remaining organic solvent may be distilled off more completely. Also, the free fatty acids and odor components contained in the recovery product may be removed at the same time.

INDUSTRIAL APPLICABILITY

The present invention made it possible to provide a powdery composition which has a high granule-forming property, and which is spherical, well flowable, not so high in bulk (specific volume), and which is heavy-duty and easy to handle and which may be obtained by adding an inorganic powdery excipient to a ground Haematococcus alga containing astaxanthin in an emulsified state in a water medium in the presence of an antioxidant and a surfactant and drying the prepared suspension as well as a process for preparing said powdery composition. The powdery composition of the present invention is subjected to an extraction treatment using an organic solvent such as acetone or the like according to the conventional process whereby astaxanthin derived from Haematococcus alga may be extracted efficiently.

Also, the astaxanthin-containing powders in the present invention is added to a feed for animals such as fishes, livestock, etc. in the form as formed whereby it can be utilized as a reviver for red colored fishes or as a color tone improving agent for meat, or it is further pulverized to fine particles whereby it may be utilized as a coloring component and an antioxidant component for cosmetics.

The invention claimed is:

1. An astaxanthin-containing powdery composition which is obtained by drying a suspension comprising a ground Haematococcus alga containing astaxanthin, a surfactant, an antioxidant, an inorganic powdery excipient and water.

2. The powdery composition as claimed in claim 1 wherein said surfactant is water soluble and has an HLB value above 7.0.

3. The powdery composition as claimed in claim 1 wherein said surfactant is one or more members selected from the group consisting of a glycerin fatty acid ester, sucrose fatty acid ester, sorbitan fatty acid ester and propylene glycol fatty acid ester.

4. The powdery composition as claimed in claim 1 wherein said antioxidant is one or more members selected from the group consisting of vitamin E (tocopherol), rosemary extract, tocotrienol and vitamin C.

5. The powdery composition as claimed in claim 1 wherein said inorganic powdery excipient is one or more selected from the group consisting of silicic anhydride, calcium hydrogen phosphate, calcium silicate and calcium phosphate.

6. The powdery composition as claimed in claim 1 wherein the drying is spray drying.

7. A process for preparing an astaxanthin-containing powdery composition which comprises drying a suspension comprising a ground Haematococcus alga containing astaxanthin, a surfactant, an antioxidant, an inorganic powdery excipient and water.

8. The process for preparing a powdery composition as claimed in claim 7 wherein the drying is conducted by a spray drying process.

9. A process for recovering astaxanthin which is characterized by extracting astaxanthin from the powdery composition as claimed in claim 1 with an organic solvent.

10. The powdery composition as claimed in claim 1, wherein the surfactant is decaglyceryl monolaurate, the antioxidant is rosemary extract and the inorganic powdery excipient is silicic anhydride.

* * * * *